(12) United States Patent
Sato

(10) Patent No.: US 11,648,012 B2
(45) Date of Patent: May 16, 2023

(54) METHOD AND BALLOON CATHETER

(71) Applicant: Takahiro Sato, Tokyo (JP)

(72) Inventor: Takahiro Sato, Tokyo (JP)

(*) Notice: Subject to any disclaimer, the term of this patent is extended or adjusted under 35 U.S.C. 154(b) by 904 days.

(21) Appl. No.: 16/426,327

(22) Filed: May 30, 2019

(65) Prior Publication Data

US 2020/0375601 A1 Dec. 3, 2020

(51) Int. Cl.
*A61B 17/12* (2006.01)
*A61M 13/00* (2006.01)
*A61B 17/00* (2006.01)
*A61M 31/00* (2006.01)
*A61B 17/068* (2006.01)
*A61M 25/10* (2013.01)
*A61B 17/04* (2006.01)

(52) U.S. Cl.
CPC .. *A61B 17/12045* (2013.01); *A61B 17/12099* (2013.01); *A61B 17/12136* (2013.01); *A61M 13/003* (2013.01); *A61M 31/00* (2013.01); *A61B 17/00491* (2013.01); *A61B 17/0469* (2013.01); *A61B 17/068* (2013.01); *A61B 2017/00827* (2013.01); *A61M 25/1011* (2013.01); *A61M 2025/1056* (2013.01); *A61M 2210/1053* (2013.01)

(58) Field of Classification Search
CPC ........ A61B 17/12045; A61B 17/12099; A61B 2017/00827; A61B 2017/00818; A61M 13/003; A61M 25/1011; A61M 2210/1053; A61M 2210/1057; A61M 2025/1052; A61F 5/0069; A61F 5/0079; A61F 5/0076
See application file for complete search history.

(56) References Cited

U.S. PATENT DOCUMENTS

| | | | | |
|---|---|---|---|---|
| 4,634,435 A | * | 1/1987 | Ingraham | A61M 25/1011 264/101 |
| 5,167,627 A | * | 12/1992 | Clegg | A61J 15/0015 604/174 |
| 9,744,025 B2 | | 8/2017 | Sato | |
| 2001/0049539 A1 | * | 12/2001 | Rehil | A61F 2/0063 606/1 |
| 2004/0143286 A1 | * | 7/2004 | Johnson | A61F 2/954 623/1.11 |
| 2012/0089157 A1 | * | 4/2012 | Forsell | A61F 5/0069 606/139 |
| 2016/0250056 A1 | * | 9/2016 | Keren | A61B 17/064 606/144 |
| 2019/0117519 A1 | * | 4/2019 | Schmid-Schonbein | A61J 15/0084 |

FOREIGN PATENT DOCUMENTS

JP 5653511 B2 1/2015

OTHER PUBLICATIONS

Katz, Philip O. et al., "Guidelines for the Diagnosis and Management of Gastroesophageal Reflux Disease." Am J Gastroenterol, 2013, 108, pp. 308-328; Cited in the Specification.

(Continued)

*Primary Examiner* — Kathleen S Holwerda
*Assistant Examiner* — Serenity A Miller
(74) *Attorney, Agent, or Firm* — WHDA, LLP

(57) ABSTRACT

There is provided with a method. A cardia and a pylorus of a stomach of a patient is blocked. The stomach is inflated. The stomach is secured within an abdominal cavity of the patient.

10 Claims, 6 Drawing Sheets

(56) References Cited

OTHER PUBLICATIONS

Sheen, Edward et al., "Adverse Effects of Long-Term Proton Pump Inhibitor Therapy", Digestive Diseases and Sciences, 2011, 56, pp. 931-950; Cited in the Specification.
Abraham, Neena S. et al., "Proton pump inhibitors: potential adverse effects", Current Opinion, Gastroenterol, Nov. 2012, vol. 28, No. 6, pp. 615-620; Cited in the Specification.
Sato Takahiro et al., "Is Laparoscopic Surgery a Contraindication in Patients with Severe Senile Kyphosis?" Hepato-Gastroenterology, 2010, 57, pp. 1095-1098; Cited in the Specification.
Sato Takahiro et al., "New and Safe Approach: Percutaneous Endoscopic Gastrostomy for the Older Patient with Gastric Cancer With Dysphagia", International Surgery, 2008, 93, pp. 206-208; Cited in the Specification.
Sato, Takahiro et al., "Improvement in a surgical method and perioperative management for a very elderly patient suffering from gastric cancer", Journal of Japan Surgical Association, 2016, 77, (3 pages), with partial English translation; Cited in the Specification.
Sato Takahiro et al., "A cardia dysfunction and a pylorus dysfunction relate", Journal of Gastroenterological Endoscopy Society, 2018, 60(Suppl.1), p. 826; with partial English translation; Cited in the Specification.
Sato, Takahiro et al., "Antero-Caudal traction of EGJ reduces Morbidity and Mortality", The Japanese Journal of Gastroenterological Surgery, 2018, p. 139; with partial English translation; Cited in the Specification.
Sato, Takahiro et al., "The Sequential Model of Barrett's Esophagus and Adenocarcinoma Induced by Duodeno-esophageal Reflux without Exogenous Carcinogens", Anticancer Research, 2002, 22, pp. 39-44; Cited in the Specification.
Miwa, Koichi et al., "Reflux of duodenal or Gastro-duodenal contents induces esophageal carcinoma in rats", International Journal of Cancer, 1996, 67, pp. 269-274; Cited in the Specification.
Sato, Takahiro et al., "Significance of Palisading Longitudinal Esophagus Vessels: Identification of theTrue Esophagogastric Junction Has Histopathological and Oncological Considerations", Digestive Diseases and Sciences, 2010, 55, pp. 3095-3101; Cited in the Specification.
Sato, Takahiro et al., "Palisading Longitudinal Esophagus Vessels at Esophago-gastric Junction", 2008, 55, pp. 305-307; Cited in the Specification.
Sato, Takahiro et al., "Endoscopic Total Layer Resection with Laparoscopic Sentinel Node Dissection and Defect Closure for Duodenal Carcinoid", Hepato-Gastroenterology, 2005, 52, pp. 678-679:Cited in the Specification.
Bais, J.E. et al., "Laparoscopic or conventional Nissen fundoplication for gastro-oesophageal reflux disease: randomised clinical trial", The Netherlands Antireflux Surgery Study Group. The Lancet, 2000, 355, pp. 170-174; Cited in the Specification.
Franzen, Thomas, "Long-term outcome is worse after laparoscopic than after conventional Nissen fundoplication." Scandinavian Journal of Gastroenterology, 2005, 40, pp. 1261-1268; Cited in the Specification.

\* cited by examiner

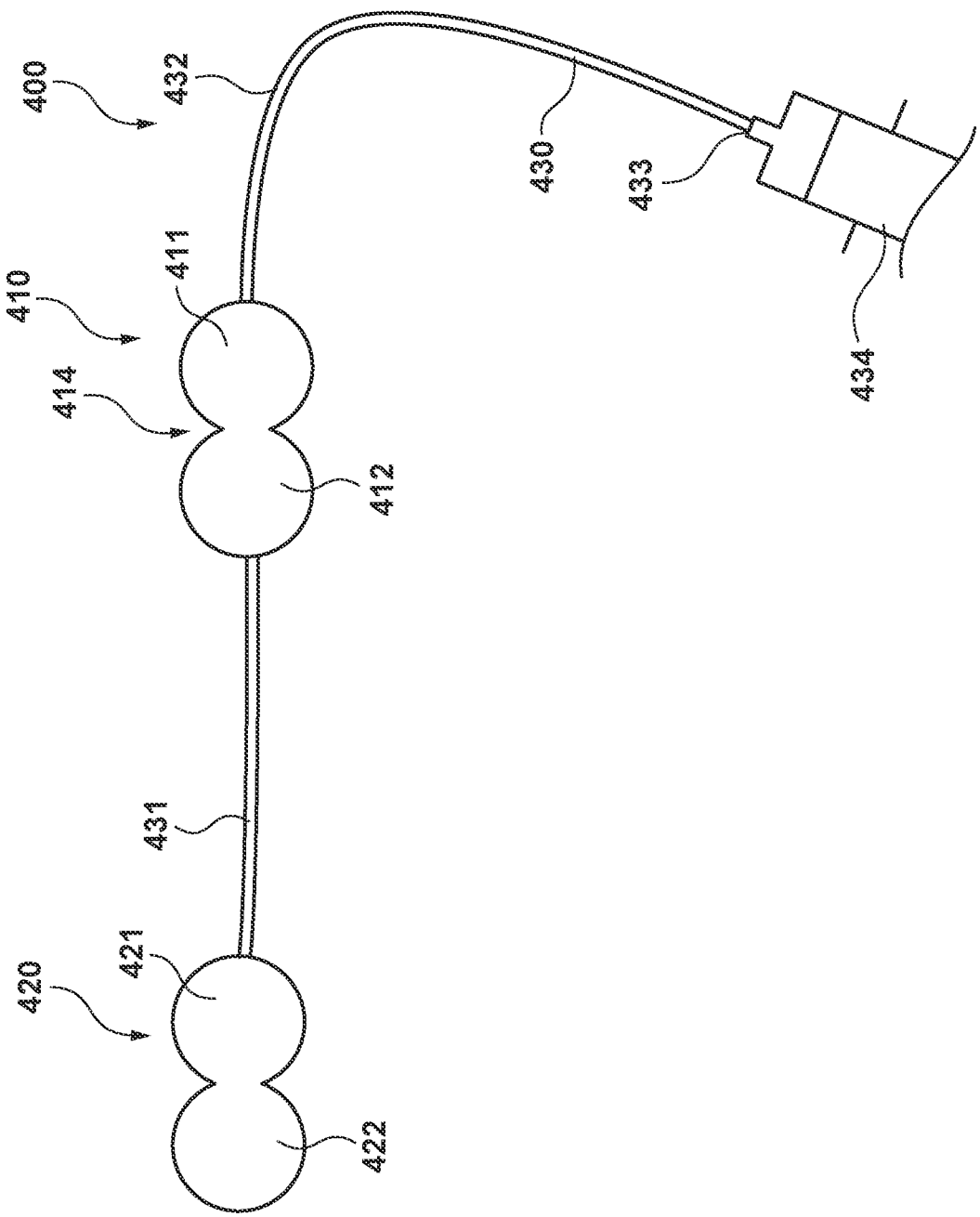

METHOD AND BALLOON CATHETER

BACKGROUND

Field

The present invention relates to a method and a balloon catheter, and more particularly to a treatment of a gastro-esophageal reflux disease.

Description of the Related Art

A gastro-esophageal reflux disease (GERD) such as reflux esophagitis refers mainly to a state where gastric acid flows into an esophagus. The GERD relates to a hiatal hernia, a lower esophageal sphincter relaxation syndrome, a metabolic syndrome, and an elevated acid secretion after a *Helicobacter pylori* eradication, and the number of patients suffering from the GERD is increasing in Japan. A PPI (proton pump inhibitor) is effective and plays an essential role in treating the GERD. However, the increasing number of the GERD patients has lead to the cost of PPI affecting the economy, especially the public healthcare insurance system. Furthermore, the safety of a long-term administration of a PPI is still being evaluated. 1) Katz P O, Gerson L B, Vela M F. "Guidelines for the diagnosis and management of gastroesophageal reflux disease." Am J Gastroenterol 2013, 108: 308-328. 2) Sheen E, Triadafilopoulo G. "Adverse effects of long-term proton pump inhibitor therapy." Dig Dis Sci 2011, 56: 931-950. 3) Abraham N S: "Proton pump inhibitors: potential adverse effects." Curr Opin Gastroenterol 2012, 28: 615-620.

The inventor has reported stabilization of the esophago-gastric junction within an abdominal cavity by pulling and fixing a jejunum to an abdominal wall in addition to a Roux-en-Y anastomosis in a patient with a round back and a patient with frequent reflux and pulmonary aspiration. 4) Sato T, et al. "Is laparoscopic surgery a contraindication in patients with severe senile kyphosis?" Hepato-gastroenterol 2010, 57: 1095-1098. 5) Sato T, et al. "New and safe approach—percutaneous endoscopic gastrostomy for the older gastric cancer patient with dysphagia." Int Surg 2008, 93: 206-208. Further, the inventor has reported improvement in pulmonary aspiration and the GERD by such pulling. 6) Sato T, et al. "Improvement in a surgical method and perioperative management for a very elderly patient suffering from gastric cancer." Journal of Japan Surgical Association, 2016, 77: S532. 7) Sato T, et al. "A cardia dysfunction and a pylorus dysfunction relate." Journal of Gastroenterological Endoscopy Society, 2018, 60(Suppl.1), 826. 8) Sato T, et al. "Antero-Caudal traction of EGJ reduces Morbidity and Mortality." The Japanese Journal of Gastroenterological Surgery, 2018, 139(Sullp.1).

So far, the inventor has clinically and experimentally studied reflux of digestive juice to esophagus, and proved that, not only inflammation but also continuation of chronic inflammation and exposure to endogenous mutagen contribute to carcinogenesis at gastroesophageal mucosa. 9) Sato T, et al. "The sequential model of Barrett's esophagus and adenocarcinoma induced by duodeno-esophageal reflux without exogenous carcinogens." Anticancer Res 2002, 22: 39-44. 10) Miwa K, et al. "Reflux of duodenal or gastro-duodenal contentents induces esophageal carcinoma in rats." Int J Cancer 1996, 67: 269-274. The inventor has also reported patentability thereof 11) Japanese Patent No. 5653511. 12) U.S. Pat. No. 9,744,025. Furthermore, the inventor have studied an the esophagogastric junction anatomically and histopathologically to prove that a palisade vessel localized at a surface of an esophageal wall which can be recognized endoscopically defines a bottom of an esophagus. 13) Sato T, et al. "Significance of palisading longitudinal esophagus vessels: Authentic identification of the esophago-gastric junction has histopathological and oncological considerations." Dig Dis Sci 2010, 55: 3095-3101. 14) Sato T, et al. "Palisading longitudinal esophagus vessels at esophago-gastric junction." 2008, 55: 305-307.

In the field of a minimally invasive therapy, the inventor has invented an original method of simultaneous laparoscopic and endoscopic surgery (LECS). 15) Sato T, et al. "Endoscopic total layer resection with laparoscopic sentinel node dissection and defect closure for duodenal carcinoid." Hepato-gastroenterol 2005, 52: 678-679. Hiatal hernia and cardiac dysfunction are causes of gastroesophageal reflux. When an esophagogastric junction enters into a thoracic cavity, gastric juice, bile, pancreatic juice, duodenal juice, and intestinal juice easily flow into an esophagus in the thoracic cavity with a negative pressure. Surgical reflux prevention operation has been performed. Recently a laparoscopic operation has been performed for minimal invasiveness, however, this operation still requires general anesthesia and may accompany complications. 16) Bais J E, Bartelsman J F, Bonjer H J, Cuesta M A, Go P M, Klinkenberg-Knol E C, van Lanschot J J, Nadorp J H, Smout A J, van der Graaf Y, Gooszen H G. "Laparoscopic or conventional Nissen fundoplication for gastro-esophageal reflux disease: randomized clinical trial." The Netherlands Antireflux Surgery Study Group. Lancet. 2000, 355: 170-174. 17) Franzen T, Anderberg B, Wiren M, Johansson K E. "Long-term outcome is worse after laparoscopic than after conventional Nissen fundoplication." Scand J Gastroenterol. 2005, 40: 1261-1268.

SUMMARY

According to an embodiment of the present invention, a method comprises: blocking a cardia and a pylorus of a stomach of a patient; inflating the stomach; and securing the stomach within an abdominal cavity of the patient.

According to another embodiment of the present invention, a balloon catheter comprises: a catheter tube; a first balloon for blocking a cardia of a stomach; and a second balloon for blocking a pylorus of the stomach.

Further features of the present invention will become apparent from the following description of exemplary embodiments (with reference to the attached drawings).

BRIEF DESCRIPTION OF THE DRAWINGS

FIGS. 4-7B schematically illustrate a balloon catheter according to an embodiment.

DESCRIPTION OF THE EMBODIMENTS

According to an embodiment of the present invention, a method comprises: blocking a cardia and a pylorus of a stomach of a patient; inflating the stomach; and securing the stomach within an abdominal cavity of the patient. In other words, the inventor conceived of securing a stomach within an abdominal cavity. Securing the stomach may be performed by, for example, fixing the stomach to an abdominal wall. The inventor also conceived of inflating the stomach to facilitate securing the stomach within the abdominal cavity. For example, inflating the stomach can facilitate pulling the stomach from the thoracic cavity into the abdominal cavity. This method may be performed endoscopically, may be easily performed, or may be less invasive. Thus, an embodiment of the present invention provides an easy or less invasive surgical method for a GERD.

The embodiments of the present invention will be described below with reference to the accompanying drawings. However, the scope of the present invention is not limited to the following embodiments.

Figure 1:
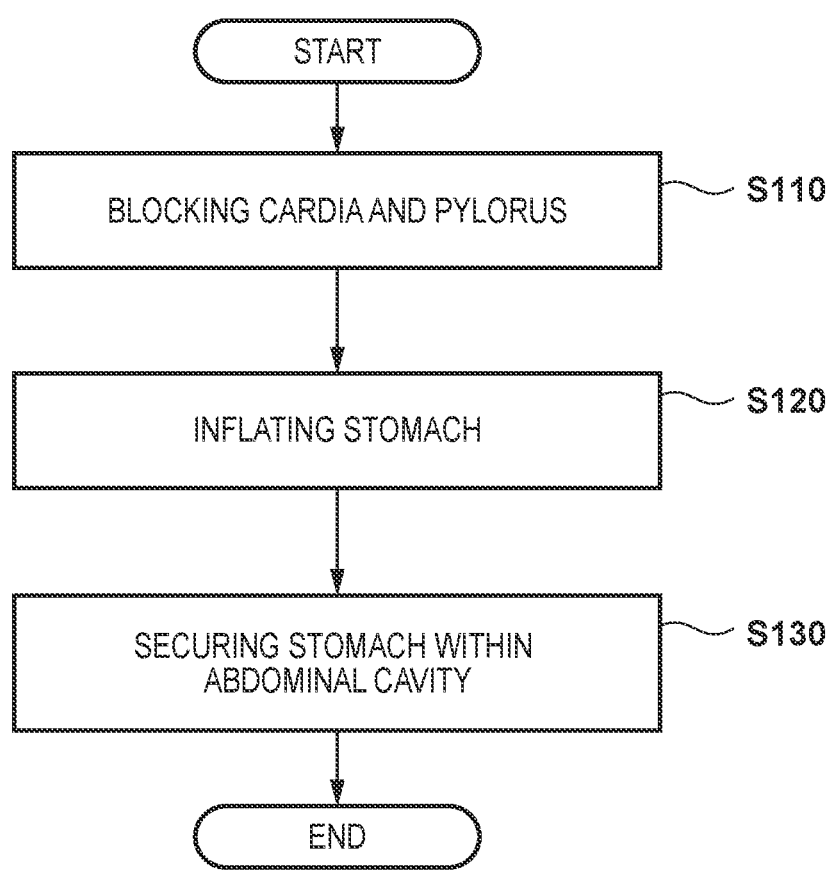
FIG. 1 is a flowchart illustrating a method according to an embodiment.

A method according to an embodiment of the present invention will be described below referring to FIG. 1. As illustrated in FIG. 1, a method according to an embodiment comprises a step S110 of blocking a cardia and a pylorus of a stomach of a patient, a step S120 of inflating the stomach, and a step S130 of securing the stomach within an abdominal cavity of the patient.

In Step S110, a cardia and a pylorus of a stomach of a patient is blocked. In an embodiment, the cardia and the pylorus is blocked to close the cardia and the pylorus, such that the stomach can be inflated by supplying a gas and/or an air into the stomach. A patient having dysfunction of the cardia, which may lead to a GERD, tends to also have dysfunction of the pylorus. Therefore, Step S110 includes blocking both of the pylorus and the stomach to completely close the stomach and to facilitate subsequent inflation of the stomach.

In an embodiment, a balloon can block the cardia and/or the pylorus. Namely, Step S110 may include placing a balloon at the cardia and the pylorus and inflating the balloon. A gastric camera such as a GTF (a gastric camera with a fiber scope) may be used to place the balloon at the cardia and/or the pylorus. However, a method for blocking the cardia and/or the pylorus is not limited thereto, and for example, a surgical clip can be used to block the cardia and/or the pylorus.

A balloon catheter can be used to place a balloon at the cardia and/or the pylorus. A typical balloon catheter may have a catheter tube and a balloon. The inside of the catheter tube and the inside of the balloon may be continuous, such that an air and/or a liquid can be supplied through the catheter tube to inflate the balloon. A surgeon can insert the balloon catheter from a mouth of the patient, through an esophagus, to the cardia and/or to the stomach and to the pylorus, while the balloon is deflated. Thus, the surgeon can place the balloon of the balloon catheter at the cardia and/or the pylorus. Thereafter, the surgeon can inflate the balloon, with a gas and/or a liquid, to block the cardia and/or the pylorus.

The balloon catheter may be a double balloon catheter. The double balloon catheter may have a first balloon and a second balloon. The first balloon is designed to block the cardia, and the second balloon is designed to block the pylorus. The double balloon catheter may have a catheter tube, and, the inside of the catheter tube, the inside of the first balloon, and the inside of the second balloon may be continuous. A surgeon can advance this double balloon catheter from the mouth to the stomach while the first balloon and the second balloon are deflated, such that the first balloon is placed at the cardia and the second balloon is at the pylorus. Subsequent supply of a gas and/or a liquid through the catheter tube will inflate the first balloon and the second balloon and close the cardia and the pylorus. An embodiment of the balloon catheter designed for this usage will be described in detail later.

Figure 2:
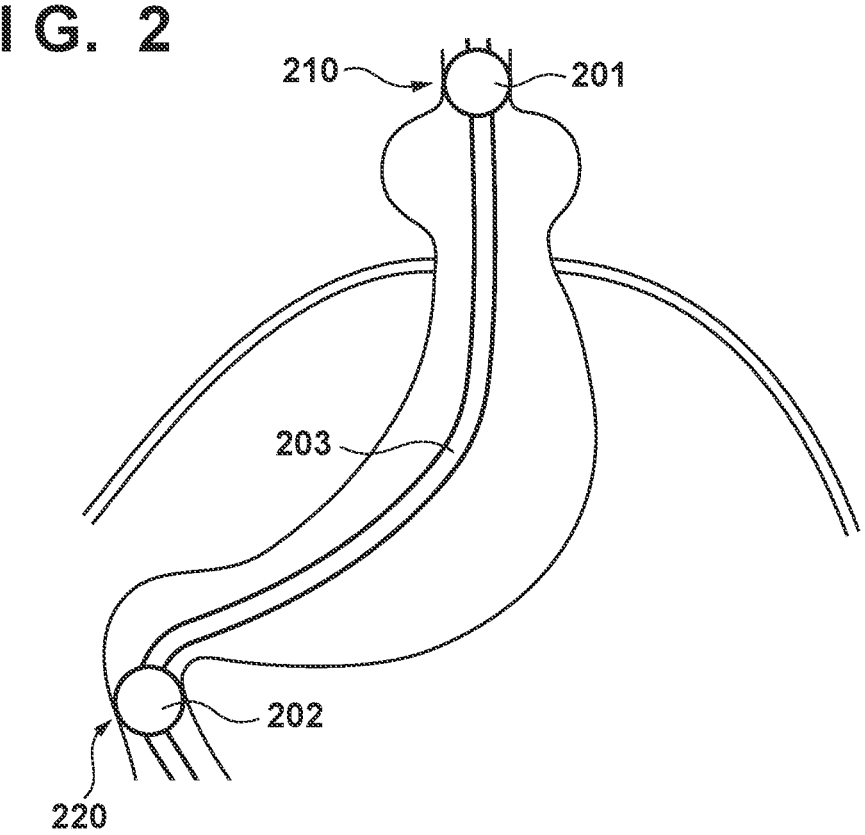
FIG. 2 is a schematic illustration explaining how to clock the cardia and the pylorus.

FIG. 2 schematically illustrates the blockage of the cardia 210 and the pylorus 220 with a double balloon catheter 200. As depicted in FIG. 2, the first balloon 201 blocks the cardia 210 and the second balloon 202 blocks the pylorus 220. The catheter tube 203 connects the first balloon 201 and the second balloon 202, and extends from the first balloon 201 through the esophagus and the mouth to the outside of the body of the patient.

In Step S120, the stomach is inflated. For example, a gas and/or a liquid may be supplied to the stomach to inflate the stomach. Since the cardia and the pylorus are blocked in Step S110, supplying the gas and/or the liquid to the stomach will inflate the stomach. In Step S120, the stomach may be overexpanded. Since the stomach is closed, a surgeon can easily deliver an air to the stomach and exhaust the air from the stomach in order to inflate or deflate the stomach. The gas and/or the liquid may be supplied to the stomach through a catheter. Namely, the catheter which extends from the mouth through the esophagus to the inside of the stomach can deliver a gas and/or a liquid, which may be an air, supplied from the outside of the body of the patient.

In an embodiment, the gas and/or the liquid is supplied to the stomach through a further catheter, which is a separate catheter from the balloon catheter. In such an embodiment, a further catheter may be inserted from a mouth of the patient to the stomach of the patient, before inflating the balloon at the cardia. The gastric camera, for example, can be used as the further catheter to deliver the gas and/or the liquid. An embodiment of the balloon catheter designed for this usage will be described in detail later.

In another embodiment, the balloon catheter to close the cardia and/or the pylorus may also be used to deliver the gas and/or the liquid to the stomach. For example, the balloon catheter may have two channels, one channel being for inflating the balloon and the other channel being for inflating the stomach. In this example, the other channel being for inflating the stomach is designed to end within the stomach, for example, between the first balloon designed to block the cardia and the second balloon designed to block the pylorus.

As explained above, a patient suffering from a GERD typically have a hiatal hernia, i.e., the stomach partly enters into a thoracic cavity through a diaphragm, and in fact this hiatal hernia will lead to a GERD. By inflating the stomach in this embodiment, the stomach spontaneously goes out of the thoracic cavity and the diaphragm into the abdominal cavity with a physical force resulting in inflation, such that the stomach inflates within a wide abdominal cavity.

In other words, inflating the stomach draws out the stomach into the abdominal cavity. Thus, the Step S120 can be effective in treating the hiatal hernia and a GERD.

In Step S130, the stomach is secured within an abdominal cavity of the patient. Although the stomach is drawn out of the thoracic cavity, a part of the stomach may return to the thoracic cavity to cause a hiatal hernia again. This Step S130 secures the stomach within an abdominal cavity to prevent the stomach from returning to the thoracic cavity again.

Figure 3:
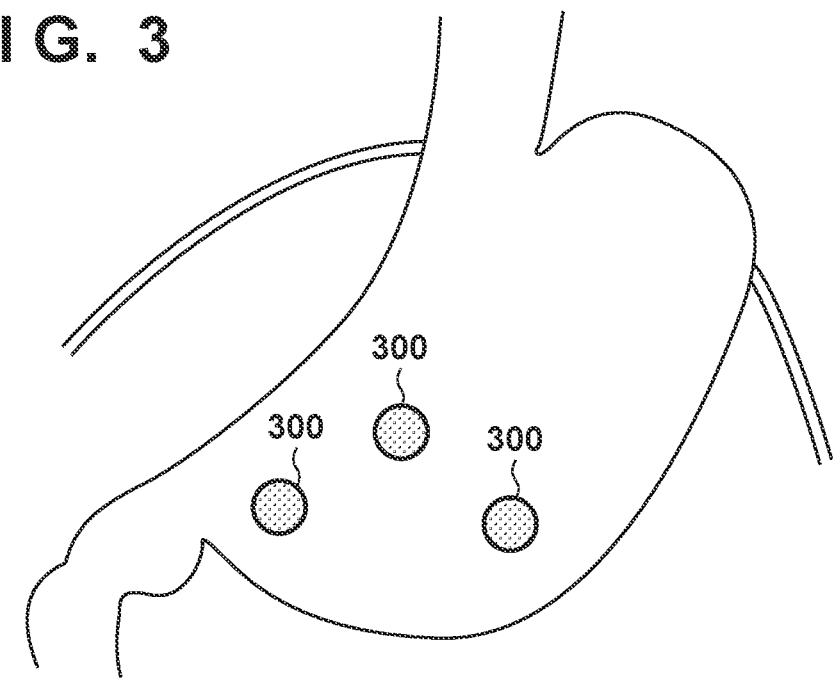
FIG. 3 is a schematic illustration explaining how to secure the stomach within the abdominal cavity.

A method for securing the stomach within the abdominal cavity is not particularly limited. For example, the stomach may be fixed to an abdominal wall, such as the anterior wall of the abdominal wall, to secure the stomach within the abdominal cavity. The fixation may be performed using a medical stapler, an adhesive, and/or a suture. In one embodiment, a surgeon can sew the abdominal wall and the wall of the stomach together, and further inject a medical adhesive between the abdominal wall and the wall of the stomach. In this embodiment, the suture can be removed after the wall of the stomach adheres to the abdominal wall. In another embodiment, a surgeon can deliver a medical stapler, for example through an endoscope, a gastric camera, or the further catheter, and staple the wall of the stomach and the abdominal wall together from the stomach. The stomach may be fixed to the abdominal wall at multiple locations. For example, the stomach can be fixed to the abdominal wall at three locations 300 as depicted in FIG. 3.

After Step S130, the blockage of the cardia and the pylorus can be removed. When a balloon catheter is used to block the cardia and/or the pylorus, the balloon can be deflated and then the balloon catheter can be removed.

A method according to an embodiment is effective in retracting the esophagogastric junction from the thoracic cavity. Thus, a method according to an embodiment is effective in preventing or reducing gastric acid flowing into an esophagus. Therefore, a method according to an embodiment is effective in treating a GERD of a patient. In other words, a method according to an embodiment can be applied to a patient suffering from a GERD. This method may also reduce a therapeutic amount of a PPI required to treat a GERD, and may possibly enable the patient to quit the PPI.

This method is simple and less invasive, namely, the blocking, the inflating, and the securing may be performed endoscopically. Therefore, this method may be performed without general anesthesia, and may be performed with local anesthesia. Thus, this method may be applied to a patient for whom there is a risk in inducing general anesthesia. Furthermore, this method may be effective in preventing or reducing gastric juice, bile, pancreatic juice, duodenal juice, or intestinal juice flowing into an esophagus, which contributes to the symptoms of a GERD but will not be effectively prevented by the PPI alone. Therefore, this method may provide a more effective treatment of a GERD, and may be applied to a GERD which is poorly controlled with a PPI.

The stomach may be detached from the abdominal wall after the treatment. For example, when a therapeutic goal is achieved, for example, when a symptom of a GERD is reduced, the stomach can be detached from the abdominal wall. This procedure may be performed laparoscopically.

As described above, a double balloon catheter may be used in a method according to an embodiment. A typical double balloon catheter comprises a catheter tube, a first balloon for blocking a cardia of a stomach, and a second balloon for blocking a pylorus of the stomach.

FIG. 4 illustrates a double balloon catheter according to an embodiment, which is particularly adapted to the method above. The balloon catheter 400 has a first balloon 410, a second balloon 420, and a catheter tube 430.

The catheter tube 430 connects to the first balloon 410 and the second balloon 420. The catheter tube 430 has a first segment 431 which connects the first balloon 410 and the second balloon 420, and a second segment 432 which extends from the proximal end 433 of the balloon catheter 400 to the second balloon 420. The first segment 431 is designed to be placed within the stomach, while the second segment 432 is designed to be placed in the esophagus. The first segment 431 and the second segment 432 may have different configurations. While in use, the second segment 432 extends from the second balloon 420 through the esophagus, the pharynx, and the mouth, to the outside of the patient.

The inside of the catheter tube 430, the inside of the first balloon 410, and the inside of the second balloon 420 are continuous, such that a gas and/or a liquid injected through the catheter tube 430 can inflate the first balloon 410 and the second balloon 420. Similarly, the gas and/or the liquid, which have been injected into the first balloon 410 and the second balloon 420, may be removed through the catheter tube 430 to deflate the first balloon 410 and the second balloon 420. The interior volume defined by the first balloon 410, the second balloon 420, and the catheter tube 430 may open only at the proximal end 433. The proximal end 433 may be connected to an injector 434 such as a syringe. The injector 434 can inject a gas and/or a liquid, such as air, from the proximal end 433 to inflate the first balloon 410 and the second balloon 420. The distal end of the double balloon catheter 400 may be at the first balloon 410.

The material of the catheter tube 430 is not specifically limited but can have a strength high enough not to be damaged while in use, and can be free from deterioration by an effect of the environment in which the catheter tube 430 is placed, for example, the mouth, the pharynx, the esophagus, and the stomach. Examples of the material of tube 130 include polyurethane, polyethylene, silicone, Teflon, and rubber.

The dimensions of the catheter tube 430 are not particularly limited, and may be adapted to the patient. As an example, the inner diameter of the catheter tube 430 may be 0.5 mm or more, and may be 1 mm or more. As further examples, the inner diameter of the catheter tube 430 may be 4 mm or less, may be 2 mm or less, and may be 1.5 mm or less. As further examples, the outer diameter of the catheter tube may be 2.5 mm or more, and may be 3 mm or more. As further examples, the outer diameter of the catheter tube 430 may be 5 mm or less, and may be 4 mm or less. Also, as examples, the thickness of the catheter tube 430 may be 0.1 mm or more, and may be 0.2 mm or more. As further examples, the thickness of the catheter tube 430 may be 1.5 mm or less, may be 1.0 mm or less, and may be 0.5 mm or less.

The length of the first segment 431 may be long enough to extend from the cardia to the pylorus. For example, the length of the first segment 431 may be 15 cm or more, while the length of the first segment 431 may be 50 cm or less. Similarly, the length of the second segment 432 may be long enough to extend from the cardia, through the esophagus, the pharynx, and the mouth, to the outside of the patient. For example, the length of the second segment 432 may be 25 cm or more, while the length of the second segment 432 may be 100 cm or less.

The first balloon 410 is designed to block the cardia when inflated. In other words, the first balloon 410 has an inflatable portion. The first balloon 410 is a member having an empty space inside. That is, the first balloon 410 can have an gas or liquid injected inside of it to expand in a radial direction of the balloon catheter 400. In addition, removing the injected gas or liquid from the first balloon 410 will deflate the first balloon 410.

The material of the first balloon 410 is not specifically limited but can have a strength high enough not to be damaged while in use, and can be free from deterioration by an effect of the environment in which the first balloon 410 is placed, for example, the stomach and the duodenum. An example of the material of the first balloon 410 include polyurethane, polyethylene, silicone, Teflon, and rubber.

The dimension of the first balloon 410 is not particularly limited, and may be adapted to the patient such that the first balloon can block the cardia. As examples, the diameter (outer diameter) of the first balloon 410 in the radial direction of the balloon catheter 400, while inflated, may be 10 mm or more, and may be 20 mm or more. As further examples, the diameter (outer diameter) of the first balloon 410 in the radial direction of the balloon catheter 400, while inflated, may be 40 mm or less, and may be 30 mm or less. shape of the first balloon 410 is not particularly limited, while the first balloon 410 may have a spherical surface so as not to reduce mechanical stimulus to the patient.

The first balloon 410 may have a plurality of inflatable portions, in order to more easily close the cardia. In FIG. 4, the first balloon 410 has a first inflatable portion 411 and a second inflatable portion 412. More specifically, the first inflatable portion 411 and the second inflatable portion 412 have a larger diameter than the valley portion 414 between the first inflatable portion 411 and the second inflatable portion 412, while the first inflatable portion 411 and the second inflatable portion 412 are inflated, as illustrated in FIG. 4. The shape of the first balloon 410 may be referred to as a dumbbell-like shape.

The first inflatable portion 411 and the second inflatable portion 412 may be designed to sandwich the cardia when inflated. These first inflatable portion 411 and the second inflatable portion 412 will securely and tightly close the cardia. Furthermore, such configurations may be effective in reducing the risk of the Mallory-Weiss syndrome, which refers to a tear at the pylorus, during the operation.

The second balloon 420 is designed to block the pylorus when inflated. The second balloon 420 may have configurations similar to the first balloon 410, and therefore the details of the second balloon 420 is omitted here. The second balloon 420 can have an gas or liquid injected inside of it to expand in a radial direction of the balloon catheter 400. In addition, removing the injected gas or liquid from the second balloon 420 will deflate the second balloon 420. Similarly to the first balloon 410, the second balloon 420 may have a plurality of inflatable portions, in order to more easily close the pylorus. In FIG. 4, similarly to the first balloon 410, the second balloon 420 has a third inflatable portion 421 and a fourth inflatable portion 422 which are designed to sandwich the pylorus when inflated.

Figure 5A:
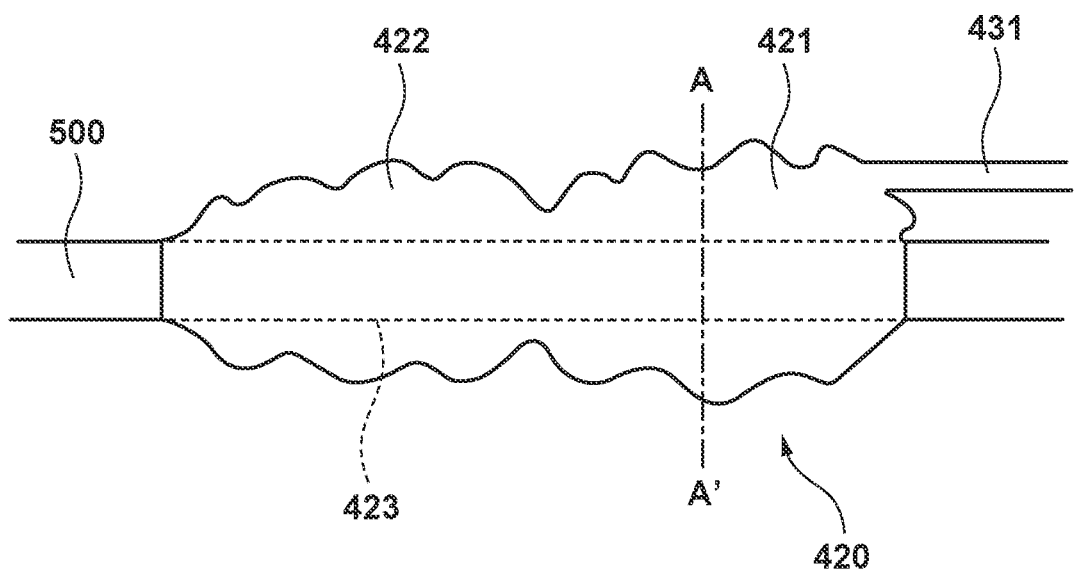
Figure 5B:
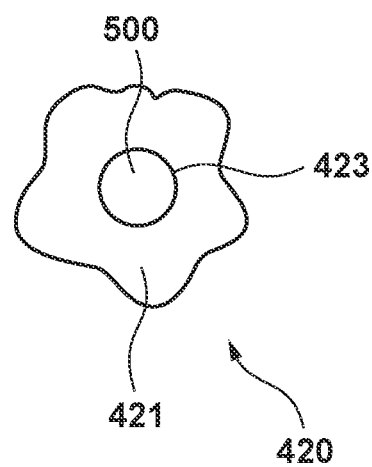

FIG. 5A is an enlarged view of an example of the second balloon 420 while the second balloon 420 is deflated. FIG. 5B is a cross-sectional view of the example of the second balloon 420 at the section A-A' while the second balloon 420 is deflated. As illustrated in FIGS. 5A and 5B, the second balloon 420 may have a second hole 423 through the second balloon 420. In other words, the second balloon 420 may have a ring-like or a cylinder-like shape such that another catheter can go through the second balloon 420. Namely, the second balloon 420 may have an outer surface which expands radially when inflated, as well as an inner surface which defines the second hole 423. As illustrated in FIG. 5A, the second hole 423 may extend in a longitudinal direction of the balloon catheter 400.

In an embodiment, the second hole 423 is designed to receive a further catheter 500 other than the catheter tube 430. This further catheter 500 may be a gastric camera as explained above which can be used to place the second balloon 420 at the pylorus. Advantages of the second hole 423 will be explained later in connection with the usage of the balloon catheter 400.

Figure 6A:
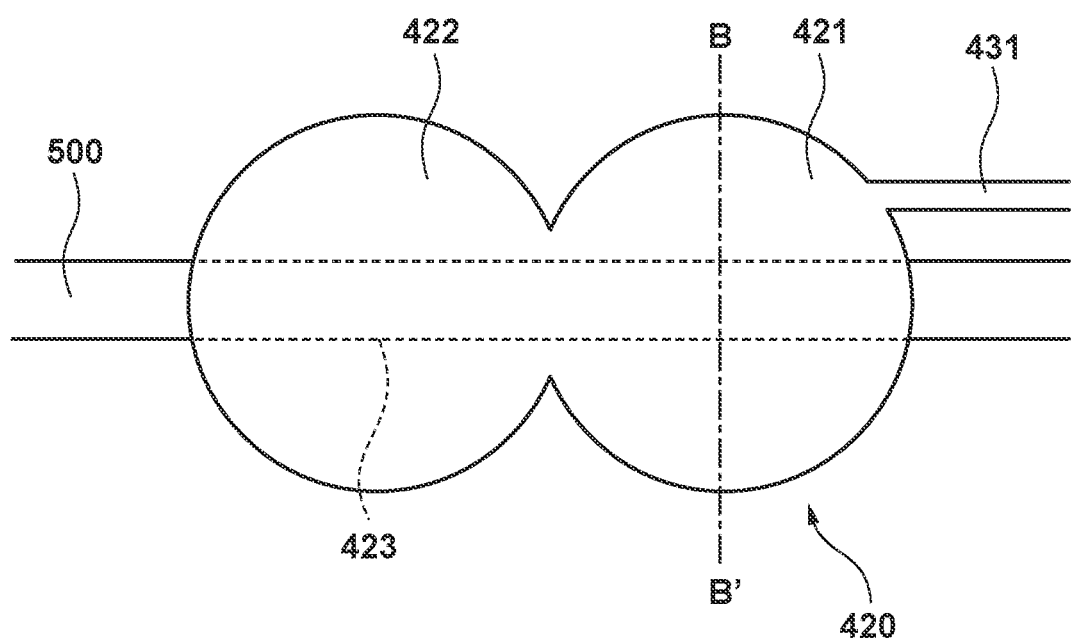
Figure 6B:
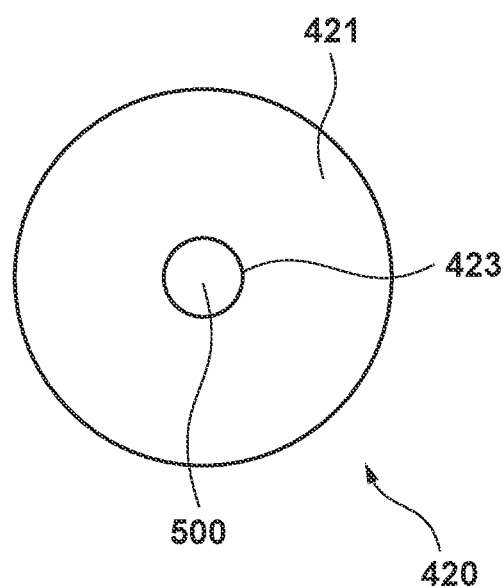

FIG. 6A is an enlarged view of the example of the second balloon 420 while the second balloon 420 is inflated and the second hole 423 receives the further catheter 500. FIG. 6B is a cross-sectional view of the example of the second balloon 420 at the section B-B'. As illustrated in FIG. 6B, the third inflatable portion 421 and the fourth inflatable portion 422 may be inflated to close the pylorus, while the second balloon 420 receives the further catheter 500 in the second hole 423. Namely, the wall of the second hole 423, i.e., the inner surface of the third inflatable portion 421 and the fourth inflatable portion 422, may tightly contact the surface of the further catheter 500, such that passage of an air though the second hole 423 may be blocked.

Figure 7A:
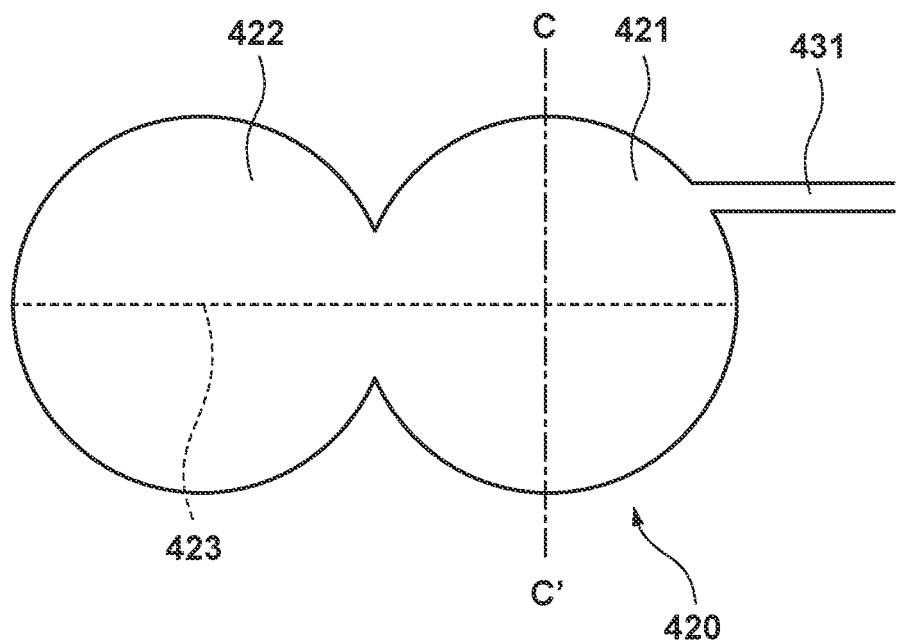
Figure 7B:
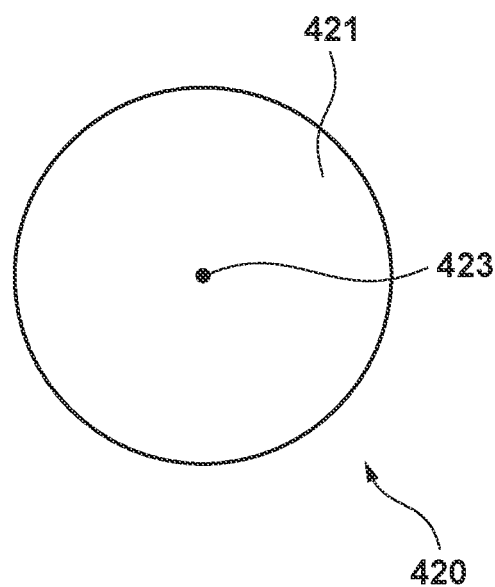

FIG. 7A is an enlarged view of the example of the second balloon 420 while the second balloon 420 is inflated and the second hole 423 does not receive the further catheter 500. FIG. 6B is a cross-sectional view of the example of the second balloon 420 at the section C-C'. As illustrated in FIG. 6B, the second balloon 420 may be designed to close the second hole 423 while the further catheter 500 is removed from the second hole 423 and the second balloon 420 is inflated. More specifically, the third inflatable portion 421 and the fourth inflatable portion 422 may close the second hole 423 while the second balloon 420 is inflated and the second hole 423 does not receive the further catheter 500. In other words, when the further catheter 500 is removed from the second balloon 420, the second hole 423 may be closed as a result of the pressure resulting from the inflated third inflatable portion 421 and the fourth inflatable portion 422.

Similarly, the first balloon 410 may have a first hole 413 through the first balloon 410, and the first hole 413 may be designed to receive a further catheter 500 other than the catheter tube 430. For example, the first inflatable portion 411 and the second inflatable portion 412 may be inflated to close the cardia, while the first balloon 410 receives the further catheter 500 in the first hole 413. Namely, the wall of the first hole 413, i.e., the inner surface of the first inflatable portion 411 and the second inflatable portion 412, may tightly contact the surface of the further catheter 500, such that passage of an air though the first hole 413 may be blocked. The first hole 413 may have configurations similar to the second hole 423, and therefore the details of the first hole 413 are omitted here.

An exemplary method for using the balloon catheter 400 in the above method as illustrated in FIG. 1 will be described below. In Step S110, the balloon catheter 400 may be inserted into the stomach, such that the first balloon 410 is placed at the cardia and the second balloon 420 is placed at the pylorus. While inserting the balloon catheter 400, the first balloon 410 and the second balloon 420 may be deflated to facilitate the insertion. Furthermore, the insertion of the balloon catheter 400 may be performed while the balloon catheter 400 receives the further catheter 500 through the first hole 413 and the second hole 423. As noted above, the further catheter 500 may be a gastric camera, which may assist in placing the first balloon 410 at the cardia and the second balloon at the pylorus.

Further in Step S110, the first balloon 410 and the second balloon 420 are inflated to block the cardia and the pylorus, respectively. Then, the first balloon 410, the second balloon 420, and the further catheter 500 may block both the cardia and the pylorus, such that the stomach can be inflated. For example, a surgeon may deliver or exhaust an air to or from the catheter tube 430 outside of the body of the patient, to inflate or deflate the first balloon 410 and the second balloon 420 to a sufficient size to close the cardia and the pylorus. When an air is delivered through the catheter tube 430, the second balloon 420 at the pylorus may inflate firstly, and the first balloon 410 at the cardia may inflate thereafter.

In Step S120, the further catheter 500 may be removed from the second balloon 420, i.e., from the second hole 423. As explained above, when the further catheter 500 is removed from the second hole 423, the second hole 423 closes such that the second balloon 420, without the further catheter 500, blocks the pylorus. The second balloon may block the pylorus water-tightly and air-tightly. A surgeon may inflate the second balloon 420 more after removing the further catheter 500 in order to more tightly close the second hole 423. After removing the further catheter 500 from the second hole 423, the first balloon 410, i.e., the first hole 413, may still receive the further catheter 500.

Then, the stomach may be inflated. In this example, an air may be provided through the further catheter 500 to the stomach to inflate the stomach. The further catheter 500, whose distal end is located between the first balloon 410 and the second balloon 420, i.e., in the stomach, may deliver an air to inflate the stomach.

In Step S130, the stomach may be secured within an abdominal cavity of the patient, as explained above. In Step S130, the first hole 413 may continue to receive the further catheter 500. The further catheter 500, such as a gastric camera, will help the surgeon to perform an operation, which may be endoscopic, to secure the stomach within the abdominal cavity.

After the operation, the first balloon 410 and the second balloon 420 may be deflated and the balloon catheter 400, as well as the further catheter 500, may be removed from the body of the patient.

A method according to an embodiment and the balloon catheter according to an embodiment may be used together with a bile duct tube and the method of placing the bile duct tube as disclosed in the U.S. Pat. No. 9,744,025, which is hereby incorporated by reference herein in its entirety. This bile duct tube can be used for treating a GERD such as reflux esophagitis, and therefore combination of the embodiments described herein and the bile duct tube disclosed in this patent will be further effective in treating a GERD.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A method comprising: inserting a balloon catheter having a first balloon and a second balloon into a stomach of a patient, such that the first balloon is placed at a cardia and the second balloon is placed at a pylorus; inflating the first balloon and the second balloon to block the cardia and the pylorus such that the stomach can be inflated when supplied with a gas and/or a liquid; supplying a gas and/or a liquid to the stomach along the balloon catheter to a volume between the first balloon and the second balloon to inflate the stomach, wherein the gas and/or the liquid is supplied at an amount enough to draw out the stomach, which partly enters into a thoracic cavity, into the abdominal cavity through inflating the stomach; and securing the stomach to an anterior wall of an abdominal wall of the patient.

2. The method according to claim 1, wherein the balloon catheter further comprises a catheter tube, wherein an inside of the catheter tube, an inside of the first balloon, and an inside of the second balloon are continuous.

3. The method according to claim 2, wherein:
the first balloon has a first hole through the first balloon, the first hole designed to receive a further catheter other than the catheter tube; and
the second balloon has a second hole through the second balloon, the second hole designed to receive the further catheter, and the second balloon is designed to close the second hole while the further catheter is removed from the second hole and the second balloon is inflated.

4. The method according to claim 1, wherein the patient suffers from gastro-esophageal reflux disease.

5. The method according to claim 1, wherein the method treats gastro-esophageal reflux disease of the patient.

6. The method according to claim 1, further comprising preventing or reducing gastric acid to flow into an esophagus.

7. A method comprising: blocking a cardia and a pylorus of a stomach of a patient; inflating the stomach; and securing the stomach within an abdominal cavity of the patient, wherein the blocking includes: inserting a balloon catheter having a first balloon and a second balloon into the stomach, such that the first balloon is placed at the cardia and the second balloon is placed at the pylorus; and
inflating the first balloon and the second balloon, wherein:
the balloon catheter further comprises a catheter tube, wherein an inside of the catheter tube, an inside of the first balloon, and an inside of the second balloon are continuous, the first balloon has a first hole through the first balloon, the first hole receiving a further catheter other than the catheter tube; and the second balloon has a second hole through the second balloon, the second hole receiving the further catheter, and the second balloon is designed to close the second hole while the further catheter is removed from the second hole and the second balloon is inflated, and wherein the inflating the stomach includes: removing the further catheter from the second hole while the first hole receives the further catheter; providing a gas and/or a liquid through the further catheter to the stomach and inflating the stomach.

8. The method according to claim 7, wherein the inflating the stomach draws out the stomach, which partly enters into a thoracic cavity, into the abdominal cavity.

9. The method according to claim 7, wherein the securing includes fixing the stomach on an abdominal wall.

10. A method comprising: blocking a cardia and a pylorus of a stomach of a patient, comprising: inserting a balloon catheter having a first balloon and a second balloon into the stomach, such that the first balloon is placed at the cardia and the second balloon is placed at the pylorus, wherein the first balloon has a first hole through the first balloon and the second balloon has a second hole through the second balloon, and the balloon catheter receiving a further catheter through the first hole and the second hole; and inflating the first balloon and the second balloon; inflating the stomach, comprising: removing the further catheter from the second hole while the first hole receives the further catheter; and providing a gas and/or a liquid through the further catheter to the stomach and inflating the stomach; and securing the stomach within an abdominal cavity of the patient.

* * * * *